United States Patent [19]

Schaefer

[11] Patent Number: 4,522,694

[45] Date of Patent: Jun. 11, 1985

[54] PROCESS FOR THE PHOTOPOLYMERIZATION OF VINYL COMPOUNDS AND PHOTOPOLYMERIZABLE MATERIALS USED IN SAID PROCESS

[75] Inventor: Roland Schaefer, Friedrichsdorf, Fed. Rep. of Germany

[73] Assignee: Kulzer & Co. GmbH, Wehrheim, Fed. Rep. of Germany

[21] Appl. No.: 568,371

[22] Filed: Jan. 5, 1984

[30] Foreign Application Priority Data

Jan. 14, 1983 [DE] Fed. Rep. of Germany ....... 3301011

[51] Int. Cl.$^3$ .............................. C08F 2/46; C08F 4/00
[52] U.S. Cl. .......................... 204/159.24; 204/159.23
[58] Field of Search ........................ 204/159.23, 159.24

[56] References Cited

U.S. PATENT DOCUMENTS

| 4,243,578 | 1/1981 | O'Sullivan et al. | 204/159.23 |
| 4,251,619 | 2/1981 | Kurita | 204/159.23 |
| 4,267,133 | 5/1981 | Kohmura et al. | 204/159.23 |

FOREIGN PATENT DOCUMENTS

| 049922 | 4/1982 | European Pat. Off. | 204/159.23 |
| 569974 | 6/1945 | United Kingdom | 204/159.23 |
| 1408265 | 10/1975 | United Kingdom | 204/159.23 |
| 1428672 | 3/1976 | United Kingdom | 204/159.23 |
| 1465897 | 3/1977 | United Kingdom | 204/159.23 |
| 2018666 | 10/1979 | United Kingdom | 204/159.23 |

Primary Examiner—Jacob Ziegler
Attorney, Agent, or Firm—Frishauf, Holtz, Goodman & Woodward

[57] ABSTRACT

A process for the production of a polymer composition comprising photopolymerizing at least one vinyl compound in the presence of a photoinitiator comprising at least one photosensitizer and at least one reducing agent selected from N-alkyl-pyrazole, N-alkyl-triazole, N-alkyl-tetrazole, N-aryl-benzotriazole, N-aryl-pyrazole, N-aryl-triazole, and N-aryl-tetrazole. Polymerizable materials and products produced by the process are also disclosed which are particularly suited as dental materials.

29 Claims, No Drawings

4,522,694

PROCESS FOR THE PHOTOPOLYMERIZATION OF VINYL COMPOUNDS AND PHOTOPOLYMERIZABLE MATERIALS USED IN SAID PROCESS

BACKGROUND OF THE INVENTION

The present invention provides a process for the photopolymerization of vinyl compounds in the presence of a photoinitiator.

Photopolymerization has many useful technical applications as, for example, the curing of lacquers and coatings in the manufacture of printing plates and in letter press printing.

Photopolymerization is also useful in the dental field as well. Photopolymerizable materials are used in the preparation of dental fillings and sealings, of crowns and bridges and artificial teeth and dentures, see, for example, British Pat. No. 569,974, DE-OS No. 31 36 484.5 corresponding to U.S. Ser. No. 413,804 filed Sept. 1, 1982, GB No. 1 428 672, U.S. Pat. Nos. 4,243,578, 4,267,133 and GB No. 2 018 666A.

British Pat. No. 1 408 265 describes photopolymerizable materials which contain as a photoinitiator a mixture of:

(a) at least one photosensitizer of the formula

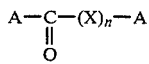

wherein X is CO, $C(R^1)(R^2)$ or $C(R^3)(OR^4)$; $R^1$, $R^2$, $R^3$, $R^4$, which may be the same or different, are hydrogen or hydrocarbyl groups; n is 0 or 1; and the groups A, which may be the same or different, are hydrocarbyl or substituted hydrocarbyl groups, and wherein the groups A may be further linked together by a direct link or by a divalent hydrocarbyl group, or in which the groups A may form a fused aromatic ring system, the groups A being aromatic or substituted aromatic groups when n is 1 and X is $C(R^1)(R^2)$ and when n is 0, and (b) at least one reducing agent capable of reducing the photosensitizer when the photosensitizer is in an excited state and having the structure

wherein M is an element of Group VB of the Periodic Table and the units R, which may be the same or different, are hydrogen atoms, hydrocarbyl groups, substituted hydrocarbyl groups or groups in which two units R together with the element M form a cyclic ring system, no more than two of the units R being hydrogen atoms or substituted hydrocarbyl groups and wherein element M is attached directly to an aromatic group R, at least one of the other units R has a

group attached to M.

British Pat. No. 1 465 897 discloses photopolymerizable materials useful in dentistry which contain as a photoinitiator a mixture of:

(a) at least one photosensitizer of the formula

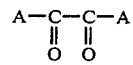

in which the groups A, which may be the same or different, are hydrocarbyl groups or substituted hydrocarbyl groups; and (b) at least one reducing agent capable of reducing the photosensitizer when the photosensitizer is in an excited state and having the formula

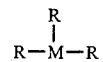

wherein M is an element of Group VB of the Periodic Table and the units R, which may be the same or different, are hydrogen atoms, hydrocarbyl groups, substituted hydrocarbyl groups, or groups in which two units R together with the element M form a cyclic ring system, no more than two of the units R being hydrogen atoms and the element M not being attached directly to an aromatic group.

The resulting mixtures can be cured by exposure to visible light or through ultraviolet rays. Examples of the photosensitizers include biacetyl, benzil, p,p'-dialkoxy benzil, benzoin, and camphorquinone. Reducing agents include propylamine, dimethylaminoethyl methacrylate, N,N'-dimethylaniline and piperidine.

European patent application No. 00 49 922 describes the use of N,N'-disubstituted cyclic 1,3-diaza compounds, particularly N,N'-disubstituted imidazolidine and hexahydropyrimidine as an accelerator in materials hardened with ultraviolet light.

German patent application No. P 31 36 484.5 describes a process for the photopolymerization of vinyl compounds in the presence of ketones and cyclic or heterocyclic compounds, particularly 5-substituted barbituric acids which are used as reducing agents.

It is an object of the present invention to provide a method of photopolymerizing vinyl compounds in the presence of a photoinitiator which comprises a carbonyl compound and an accelerator or a reducing agent. The method provides a rapid curing of the vinyl compound by means of irradiation with either ultraviolet light or visible light. The resulting polymers produced according to the present invention have excellent color fastness.

SUMMARY OF THE INVENTION

The present invention provides a process for the photopolymerization of vinyl compounds in the presence of a photoinitiator comprising:

(a) a photosensitizer comprising:

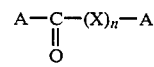

wherein X is selected from CO, $C(R^1)(R^2)$ or $C(R^3)(OR^4)$; $R^1$, $R^2$, $R^3$, $R^4$ are each selected from hydrogen and a hydrocarbon radical;
n is 0 or 1;
A are hydrocarbon radicals which may be substituted and which may be bonded together, with the proviso that when n is 1 and X is C(R¹)(R²), and when n is 0, then A is an aromatic radical; and (b) at least one reducing agent selected from the following group: N-alkyl-pyrazole, N-alkyl-triazole, N-alkyl-tetrazole, N-aryl-benzotriazole, N-aryl-pyrazole, N-aryl-triazole, and N-aryl-tetrazole, wherein the alkyl group contains 1 to 10 (and preferably 1 to 5) carbon atoms. The aryl groups are preferably selected from phenyl, naphthyl, substituted phenyl and substituted naphthyl.

It is particularly desirable to use a diketone, preferably camphorquinone, as the photosensitizer. It is also desirable to use a mixture of camphorquinone and a 2,2-dialkoxy-1,2-diphenylethanone, preferably 2,2-dimethoxy-1,2-diphenylethanone as the photosensitizer. The aforementioned sensitizers are preferably employed with a reducing agent selected from the following group: 1-aryl-pyrazolone-(5), 2-aryl-2H-benzotriazole, 1-alkyl-1H-tetrazole, and 1-aryl-1H-tetrazole. The preferred reducing agents are 1-phenyl-3-methyl-pyrazolone-(5), 1-phenyl-3,4-dimethyl-pyrazolone-(5), 2-(2-acetoxy-3,5-di-tert.-pentylphenyl)-2H-benzotriazole, 1,5-dimethyl-1H-tetrazole and 1-phenyl-5-acetylthio-1H-tetrazole.

When polymerizing esters of acrylic or methacrylic acids, it is particularly desirable to use 1-aryl-pyrazolone-(5) or 2-aryl-2H-benzotriazole as the reducing agent.

The rate of photopolymerization in accordance with the method of the present invention is similar to the rate of photopolymerization described in British Pat. No. 1 408 265. However, the vinyl polymers and copolymers obtained by the present method have superior color fastness.

The present process is applicable wherever monomer vinyl compounds, or compositions containing these compounds, can be photopolymerized by exposure to visible light and/or ultraviolet light.

The vinyl compounds which may be polymerized in accordance with the present invention include all commonly used ethylene-like unsaturated compounds, especially acrylic and methacrylic acid esters with monohydric and polyhydric alcohols. Also included are the so-called urethane acrylates and methacrylates as disclosed in U.S. Pat. No. 3,825,518 incorporated herein by reference and bis-GMA, as shown in U.S. Pat. No. 3,066,112 incorporated herein by reference, which is the reaction product of bis-phenol-A and glycidylmethacrylate,*

* bis-[4-(2-hydroxy-3-methacryloyloxypropoxy)-phenyl]-dimethylmethan.

In practice, the photosensitizer is added to the vinyl compounds or to a composition containing the vinyl compounds in an amount of between 0.01 and 10% by weight of the vinyl compounds. The preferred amount is between 0.1 and 5% by weight. The reducing agent can be provided in an amount within the same range as the photosensitizer.

The application of the process according to the present invention is especially beneficial in the field of dentistry, for the preparation of dental fillings and sealings, as well as crowns, bridges and artificial teeth and dentures by the polymerization of acrylic acid esters and/or methacrylic acid esters and, in certain cases, in the presence of materials containing inorganic fillers, by exposure to ultraviolet or visible light.

The following examples are submitted for the purpose of illustrating the invention and are not intended to limit the invention covered by the claims appended hereto. The thickness of the resulting solid body of the polymer serves as the means of evaluating the activity of the photoinitiator.

EXAMPLES 1 TO 5

A mixture of 7 grams bis-GMA, 3 grams triethyleneglycoldimethacrylate, 30 grams lithium aluminum silicate (85% by weight of which comprise particles smaller than 15 micrometers), 1 gram aluminum oxide with particle size less than 5 micrometers, and X photoinitiator (see Table 1)

is placed in a tube (inside diameter 6 mm and height 10 mm) of Delrin, a trademarked product made of a polyacetal plastic, covered with mylar foil, and irradiated for 20 seconds by a Translux-brand tungsten halogen lamp manufactured by Kulzer & Company GmbH, whose lens or window is placed on the mylar foil. The portion of the mixture which remains unpolymerized is then removed, and the thickness of the layer of the polymerized portion is measured.

The type and quantity of the photoinitiator and the thickness of the polymerized layer are shown in Table 1.

TABLE 1

| Example | Photoinitiator | Weight % | Layer Thickness (mm) |
|---|---|---|---|
| 1 | camphorquinone | 0.1 | 5.3 |
|  | + |  |  |
|  | 2,2-dimethoxy-1,2-diphenylethanone | 0.3 |  |
|  | + |  |  |
|  | 1-phenyl-3-methyl-pyrazolone-(5) | 0.1 |  |
| 2 | camphorquinone | 0.1 | 5.7 |
|  | + |  |  |
|  | 2,2-dimethoxy-1,2-diphenylethanone | 0.3 |  |
|  | + |  |  |
|  | 1-phenyl-3,4-dimethyl-pyrazolone-(5) | 0.1 |  |
| 3 | camphorquinone | 0.1 | 6.1 |
|  | + |  |  |
|  | 2,2-dimethoxy-1,2-diphenylethanone | 0.3 |  |
|  | + |  |  |
|  | 2-(2-acetoxy-3,5-di-tert.-pentyl-phenyl)-2H—benzotriazole | 0.1 |  |
| 4 | camphorquinone | 0.1 | 4.8 |
|  | + |  |  |
|  | 2,2-dimethoxy-1,2-diphenylethanone | 0.3 |  |
|  | + |  |  |
|  | 1,5-dimethyl-1H—tetrazole | 0.1 |  |
| 5 | camphorquinone | 0.1 | 6.0 |
|  | + |  |  |
|  | 2,2-dimethoxy-1,2-diphenylethanone | 0.3 |  |
|  | + |  |  |
|  | 1-phenyl-5-acetylthio-1H—tetrazole | 0.1 |  |

In the formula representing the photosensitizer A and $R^1$ to $R^4$ are the same as defined in British Pat. No. 1 408 265 which corresponds to U.S. Pat. No. 4,071,424.

I claim:

1. In a method for the production of a polymer composition comprising photopolymerizing at least one vinyl compound in the presence of a photoinitiator, the improvement comprising polymerizing said at least one vinyl compound in the presence of a photoinitiator comprising:

(a) at least one photosensitizer of the formula

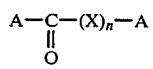

wherein

X is selected from the group consisting of CO, C(R$^1$)(R$^2$) and C(R$^3$)(OR$^4$), wherein R$^1$, R$^2$, R$^3$, R$^4$ are each selected from the group consisting of hydrogen and a hydrocarbon radical;

n is 0 or 1; and

A are hydrocarbon radicals which may be substituted and which may be bonded together with the proviso that when n is 1 and X is C(R$^1$)(R$^2$), and when n is 0, A is an aromatic radical; and (b) at least one reducing agent selected from the group consisting of N-alkyl-pyrazole, N-alkyl-triazole, N-alkyl-tetrazole, N-aryl-benzotriazole, N-aryl-pyrazole, N-aryl-tetrazole, and N-aryl-triazole.

2. The method of claim 1, wherein said reducing agent is selected from the group consisting of 1-aryl-pyrazolone-(5) 2-aryl-2H-benzotriazole, 1-alkyl-1H-tetrazole, and 1-aryl-1H-tetrazole.

3. The method of claim 1 wherein said at least one photosensitizer is a diketone compound.

4. The method of claim 3, wherein the photosensitizer comprises camphorquinone.

5. The method of claim 4, wherein the photosensitizer further comprises 2,2-dialkoxy-1,2-diphenylethanone.

6. The method of claim 5, wherein the photosensitizer further comprises 2,2-dimethoxy-1,2-diphenylethanone.

7. The method of claim 2, wherein said reducing agent is selected from the group consisting of 1-phenyl-3-methylpyrazolone-(5), 1-phenyl-3,4-dimethyl-pyrazolone-(5), 2-(2-acetoxy-3,5-di-tert.-pentyl-phenyl)-2H-benzotriazole, 1,5-dimethyl-1H-tetrazole and 1-phenyl-5-acetylthio-1H-tetrazole.

8. The method of claim 1, wherein said at least one photosensitizer and said at least one reducing agent are each present in an amount of between 0.01 and 10% by weight based on the weight of said at least one vinyl compound.

9. The method of claim 8, wherein said at least one photosensitizer and said at least one reducing agent are present in an amount between 0.1 and 5% by weight based on the weight of said at least one vinyl compound.

10. In a method for the production of a polymer composition comprising photopolymerizing at least one vinyl compound in the presence of a photoinitiator, the improvement comprising polymerizing said at least one vinyl compound in the presence of at least one diketone compound and at least one reducing agent selected from the group consisting of 1-aryl-pyrazolone-(5), 2-aryl-2H-benzotriazole, 1-alkyl-1H-tetrazole, and 1-aryl-1H-tetrazole, wherein said diketone compound and said at least one reducing agent are each present in an amount between 0.01 and 10% by weight based on the weight of said at least one vinyl compound.

11. The method of claim 10, wherein the photosensitizer comprises camphorquinone.

12. The method of claim 11, wherein the photosensitizer further comprises 2,2-dialkoxy-1,2-diphenylethanone.

13. The method of claim 12, wherein the photosensitizer further comprises 2,2-dimethoxy-1,2-diphenylethanone.

14. The method of claim 11, wherein said reducing agent is selected from the group consisting of 1-phenyl-3-methylpyrazolone-(5), 1-phenyl-3,4-dimethyl-pyrazolone-(5), 2-(2-acetoxy-3,5-di-tert.-pentyl-phenyl)-2H-benzotriazole, 1,5-dimethyl-1H-tetrazole and 1-phenyl-5-acetylthio-1H-tetrazole.

15. The method of claim 14, wherein said at least one photosensitizer and said at least one reducing agent are each present in an amount between 0.1 and 5% by weight based on the weight of said at least one vinyl compound.

16. The polymer composition produced by the method of claim 1.

17. A photopolymerizable material comprising at least one vinyl compound and a photoinitiator, said photoinitiator comprising:

(a) at least one photosensitizer of the formula

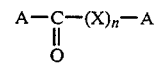

wherein

X is selected from the group consisting of CO, C(R$^1$)(R$^2$) and C(R$^3$)(OR$^4$), wherein R$^1$, R$^2$, R$^3$, R$^4$ are each selected from the group consisting of hydrogen and a hydrocarbon radical;

n is 0 or 1; and

A are hydrocarbon radicals which may be substituted and which may be bonded together with the proviso that when n is 1 and X is C(R$^1$)(R$^2$), and when n is 0, A is an aromatic radical; and (b) at least one reducing agent selected from the group consisting of N-alkyl-pyrazole, N-alkyl-triazole, N-alkyl-tetrazole, N-aryl-benzotriazole, N-aryl-pyrazole, N-aryl-tetrazole, and N-aryl-triazole.

18. The photopolymerizable material of claim 17, wherein said reducing agent is selected from the group consisting of 1-aryl-pyrazolone-(5), 2-aryl-2H-benzotriazole, 1-alkyl-1H-tetrazole, and 1-aryl-1H-tetrazole.

19. The photopolymerizable material of claim 17, wherein said at least one photosensitizer is a diketone compound.

20. The photopolymerizable material of claim 19, wherein the photosensitizer comprises camphorquinone.

21. The photopolymerizable material of claim 20, wherein the photosensitizer further comprises 2,2-dialkoxy-1,2-diphenylethanone.

22. The photopolymerizable material of claim 21, wherein the photosensitizer further comprises 2,2-dimethoxy-1,2-diphenylethanone.

23. The photopolymerizable material of claim 18, wherein said reducing agent is selected from the group consisting of 1-phenyl-3-methyl-pyrazolone-(5), 1-phenyl-3,4-dimethyl-pyrazolone-(5), 2-(2-acetoxy-3,5-di-tert.-pentylphenyl)-2H-benzotriazole, 1,5-dimethyl-1H-tetrazole and 1-phenyl-5-acetylthio-1H-tetrazole.

24. The photopolymerizable material of claim 17, wherein said at least one photosensitizer and said at least one reducing agent are present in an amount of between 0.01 and 10% by weight based on the weight of said at least one vinyl compound.

25. The photopolymerizable material of claim 24, wherein said at least one photosensitizer and said at least one reducing agent are present in an amount between 0.1 and 5% by weight based on the weight of said at least one vinyl compound.

26. The photopolymerizable material of claim 25, wherein said at least one vinyl compound is selected from the group consisting of acrylic acid esters and methacrylic acid esters.

27. The photopolymerizable material of claim 26, wherein said reducing agent is selected from the group consisting of 1-aryl-pyrazolone-(5) and 2-aryl-2H-benzotriazole.

28. The photopolymerizable material of claim 26, wherein said reducing agent is selected from the group consisting of 1-phenyl-3-methyl-pyrazolone-(5) and 1-phenyl-3,4-dimethyl-pyrazolone-(5).

29. The method of claim 11, wherein said at least one photosensitizer and said at least one reducing agent are each present in an amount between 0.1 and 5% by weight based on the weight of said at least one vinyl compound; wherein said at least one vinyl compound is selected from the group consisting of acrylic acid esters and methacrylic acid esters; and wherein said reducing agent is selected from the group consisting of N-alkyl pyrazole and N-aryl pyrazole.

* * * * *